United States Patent
Ostermaier et al.

(10) Patent No.: US 6,248,926 B1
(45) Date of Patent: Jun. 19, 2001

(54) RECOVERY OF HEXAMETHYLENEDIAMINE (HMD) WITH LOW POLAROGRAPHICALLY REDUCIBLE IMPURITIES (PRI) FROM MIXTURES OF HMD, AMINOCAPRONITIRLE AND PRI

(75) Inventors: John J. Ostermaier; Leon S. Scott, both of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/697,691

(22) Filed: Oct. 26, 2000

(51) Int. Cl.⁷ ..................... C07C 209/48; C07C 209/84; C07C 209/86

(52) U.S. Cl. ............................... 564/492; 564/498

(58) Field of Search ...................................... 564/492, 498

(56) References Cited

U.S. PATENT DOCUMENTS 5,961,788 * 10/1999 Ostermaier ............................. 203/37

* cited by examiner

Primary Examiner—Johann Richter
Assistant Examiner—Brian J. Davis

(57) ABSTRACT

A method for separating a mixture of hexamethylenediamine, aminocapronitile and polarographically reducible impurities using fractional distillation in which the temperature in the rectifying zone of a distillation column varies sigmoidally along its length to force a major portion of the PRI to co-distill with the aminocapronitrile.

1 Claim, 2 Drawing Sheets

RECOVERY OF HEXAMETHYLENEDIAMINE (HMD) WITH LOW POLAROGRAPHICALLY REDUCIBLE IMPURITIES (PRI) FROM MIXTURES OF HMD, AMINOCAPRONITIRLE AND PRI

BACKGROUND OF THE INVENTION

Nylon 6,6 is produced from two chemical ingredients, hexamethylenediamine (HMD) and adipic acid (AA). The HMD is, in turn, produced by the hydrogenation of adiponitrile (ADN). ADN is a linear alpha, omega dinitrile containing 6 carbon atoms. In the conversion of ADN to HMD, a major intermediate formed is aminocapronitrile (ACN), which has a nitrile group at one end of the molecule and an amine group at the other. Another intermediate that is formed is tetrahydroazipine (THA), which is formed by the addition of one molecule of hydrogen to ACN, followed by cyclization and elimination of ammonia. THA also exists as various oligomers with other molecules present in the system, such as HMD and ACN, and this mixture of THA and its oligomers is collectively referred to as "polarographically reducible impurities" (PRI), since analysis for the mixture is done by electrochemical reduction using a dropping mercury electrode. The presence of PRI in the HMD is undesirable, because it causes the Nylon 6,6 polymer to be of inferior quality. When HMD is produced by completely or nearly completely hydrogenating ADN, most of the THA is hydrogenated to hexamethyleneimine (HMI), which is easily removed from the HMD by distillation. The amount of PRI that exists in the crude HMD immediately following hydrogenation is less than 50 ppm, and can be controlled to acceptable levels in the refined HMD by normal distillation.

It is possible to produce Nylon 6 using ACN as the monomer. The ACN can, in turn, be manufactured using the same equipment used to produce HMD. The only required change in processing is to partially hydrogenate, rather than completely hydrogenate, the ADN to produce a mixture of ACN and HMD, together with some unreacted ADN. When this is done, there is a greater than 30 fold increase in the level of PRI in the crude hydrogenation product. This is because under partial hydrogenation conditions a much smaller portion of the PRI is hydrogenated to HMI. In order to manufacture polymer grade HMD and ACN, it is necessary to remove the PRI from both products. U.S. Pat. No. 5,961,788 describes a process for removing PRI from ACN using reactive distillation with caustic.

In order to develop a commercially acceptable process to co-produce polymer grade HMD and ACN, it is necessary to find a way to force almost all of the PRI to co-distill with the ACN, thereby producing HMD that has an acceptable level of PRI. There is a need, therefore, for a distillation process that allows the recovery of HMD that is substantially free of PRI, and which causes substantially all of the PRI to co-distill with the ACN.

SUMMARY OF THE INVENTION

This need is met by the present invention, which is a process for separating HMD from a feed mixture comprising HMD, ACN and PRI, said process comprising:

a. introducing the feed mixture into a distillation column at a feed point located therein;

b. withdrawing from a distillate withdrawal point, located above the feed point, a distillate which comprises HMD, and which further comprises at most a minor portion of the PRI which is fed to the column in the feed mixture, the locations of the feed point and the distillate withdrawal point defining a rectifying zone of the column having a length which extends between the feed point and the distillate withdrawal point and a temperature which varies along the length; and c. withdrawing from a bottoms withdrawal point, located below the feed point, a bottoms which comprises ACN, substantially free of HMD, and which further comprises a major portion of the PRI fed to the column in the feed mixture;

provided that the process is carried out while the temperature in the rectifying zone of the column varies sigmoidally along the length of the rectifying zone.

BRIEF DESCRIPTION OF THE DRAWING

The drawing consists of two figures.

DETAILED DESCRIPTION OF THE INVENTION

A mixture containing only HMD and ACN can be separated by feeding the mixture into an appropriately designed fractional distillation column, and taking HMD overhead from a distillate withdrawal point as distillate, and taking ACN from a bottoms withdrawal point as bottoms. An appropriately designed distillation column will contain a multiple number of so-called theoretical stages. The degree of HMD/ACN separation will be dependent on the number of theoretical stages employed. The higher the degree of separation, the greater the number of theoretical stages are required.

An optimized column for a desired degree of HMD/ACN separation has the minimum number of theoretical stages in the so-called rectifying zone of the column (the portion of the column between the feed point and the distillate withdrawal point) and the minimum number of stages in the so-called stripping zone of the column (the portion of the column between the feed point and the bottoms withdrawal point) required to provide the desired percentage of ACN going into the distillate, and the desired percentage of HMD going into the bottoms. A graph showing temperature (or ACN composition) versus theoretical stage for such a column would show steep temperature and composition gradients immediately above and below the theoretical stage associated with the feed point. If one were to use the same column to separate a mixture of HMD and ACN that also contains PRI, the PRI would distribute in such a way that the level of PRI in the HMD distillate would be unacceptably high.

The present invention involves the discovery that if theoretical stages are added to the rectfiying zone of a distillation column in excess of the minimum required for any desired degree of HMD/ACN separation, and the column is operated in a manner that keeps the HMD and ACN compositions of both the distillate and bottoms the same as they would be in a column with the minimum number of theoretical stages in the rectifying zone for the desired degree of HMD/ACN separation, it is possible to significantly reduce the PRI content of the distillate. The number of excess stages must be more than one, and preferably more than five. Designing and operating the column in this manner causes the ACN composition associated with these extra stages in the rectifying zone to vary only slightly, and causes a much lower temperature gradient over these excess stages than would be observed for a column with only the minimum number of stages for the desired degree of separation. A graph of column temperature versus theoretical stage (in which the top stage of the column is at the 0 point of the x-axis) for a column with excess theoretical stages in the rectifying zone, operating properly for PRI removal, shows a sigmoidal shape (i.e., shaped like the letter "S") in the section of the graph depicting the temperature of the rectifying zone.

Figure 1:
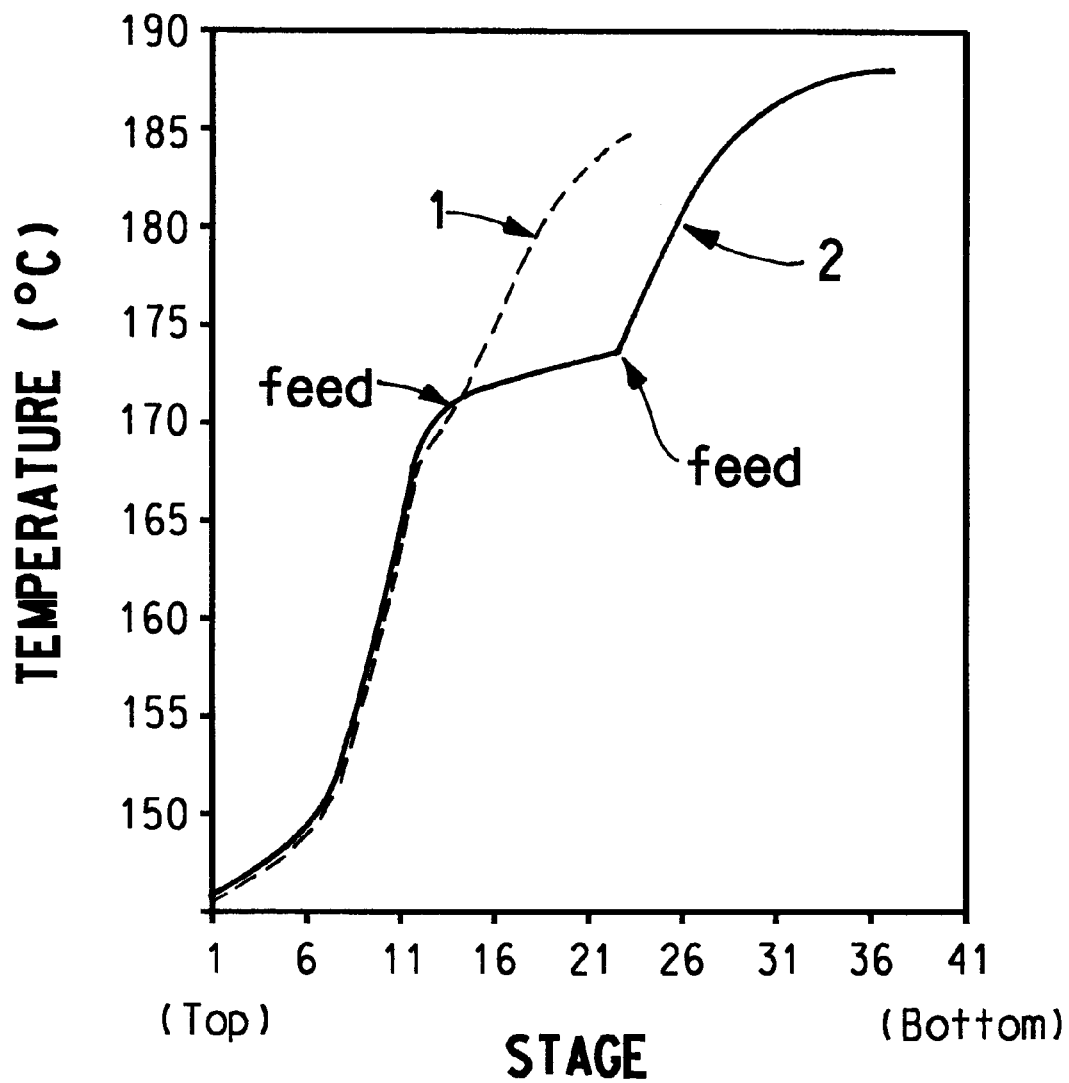
FIG. 1 is a graph showing two curves. Curve 1 is a computer-generated graph showing temperature versus theoretical stage for a hypothetical column optimized for a desired degree of HMD/ACN separation. Curve 2 shows temperature versus theoretical stage for the same column when the number of theoretical stages in its rectifying zone is increased to force PRI to co-distill with ACN as bottoms.

Turning now to FIG. 1, there is shown a graph of temperature versus theoretical stage for a column optimized for a desired HMD/ACN separation (curve 1). There is also shown a graph of temperature versus theoretical stage for a column which has excess theoretical stages in the rectifying zone and which is operated to force PRI to co-distill with the ACN in the bottoms (curve 2). The ACN composition profiles for these two columns (not shown in FIGS. 1 and 2) have a similar shape, with the concentration of ACN increasing from top to bottom of the column. Without wishing to be bound by any particular theory of operation, it is believed that when a distillation column is designed to have excess theoretical stages in its rectifying zone over the number required for a desired degree of HMD/ACN separation, and the column is operated in a manner to provide a sigmoidal temperature versus theoretical stage profile in its rectifying zone, there is an increase in the level of ACN at the stages above the feed point, and this additional ACN acts as an extracting agent to wash the PRI down the column and reduce the amount of PRI in the distillate. Thus, it is believed that the mode of column operation in accordance with the present invention causes the ACN contained in the feed to act as an in situ extraction agent for the removal of PRI from HMD.

If one uses a column in which there is a number of theoretical stages in the rectifying zone in excess over the minimum number of stages required for any desired degree of HMD/ACN separation, it is possible to operate the column to increase the degree of HMD/ACN separation, or to operate the column to force the PRI to co-distill with the ACN in the bottoms.

Figure 2:
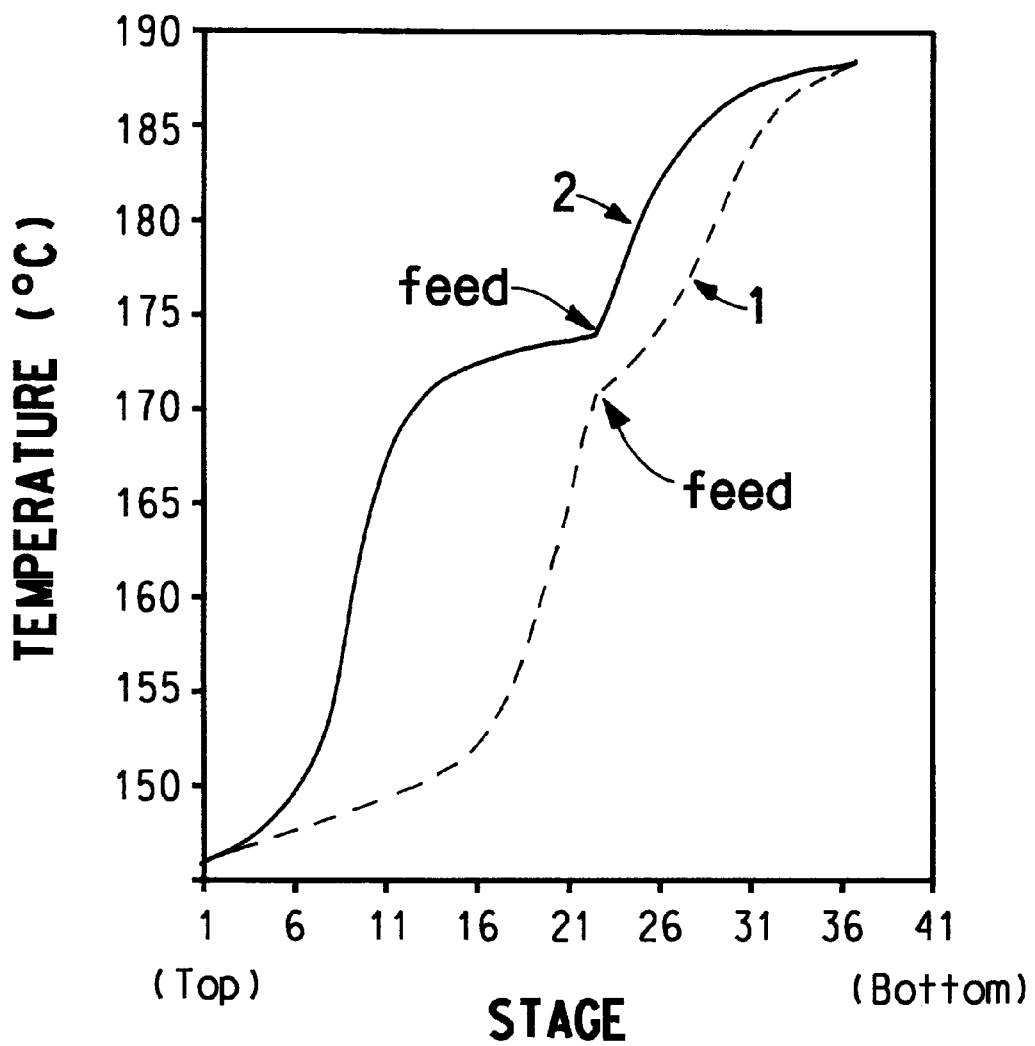
FIG. 2 is a graph showing two curves, both characterizing a hypothetical column having a number of theoretical stages in its rectifying zone in excess of that required for a desired degree of HMD/ACN separation. Curve 1 shows temperature versus theoretical stage for the column operated to minimize the amount of ACN in the distillate. Curve 2 shows temperature versus theoretical stage for the column operated to force PRI to co-distill with ACN as bottoms.

Turning now to FIG. 2, there is shown two temperature versus theoretical stage graphs for a distillation column operating for the separation of HMD from ACN. Curve 1 is a graph characterizing the column if it is operated to achieve a minimum concentration of ACN in the distillate. Curve 2 is a graph characterizing the column if it is operated to achieve reduced levels of PRI in the distillate (force the PRI to co-distill with the ACN in the bottoms). Curve 2 shows a noticeable flattening of the temperature profile just above the feed point (reduction of the slope of the curve at the feed point), which gives a temperature versus theoretical stage-in-the-rectifying-zone graph the sigmoidal shape required for PRI removal from the HMD distillate.

To achieve minimum ACN in the distillate of the column operation characterized by curve 1 of FIG. 2, one would control the rate of distillate withdrawal to maintain stage 20 at a temperature of 160 C. To achieve minimum PRI in the distillate of the column operation characterized by curve 2 of FIG. 2, one would control the rate of distillate withdrawal to maintain stage 9 at a temperature of 160 C. or stage 20 at 172. When the sigmoidal temperature profile is established, as depicted in curve 2, the temperature of any stage in the column is increased relative to what it would be when the sigmoidal shape is absent. This increase in temperature corresponds to an increase in ACN concentration on a given stage.

Thus, by varying the rate of distillate withdrawal from the column to obtain a sigmoidal temperature variation along the length of the rectifying zone, it is possible to reduce significantly the amount of PRI in the distillate relative to the removal that can be achieved when a sigmoidal temperature profile does not exist in the rectifying zone.

A column suitable for practicing the present invention can be designed by computer modeling using well-known software for this purpose, such as the software sold under the trademark "ASPEN" (Aspen Technologies, Inc., Ten Canal Park, Cambridge, Mass., USA). Generally, one may design a column having the minimum number of theoretical stages for a desired degree of HMD/ACN separation, taking into account the composition of the feed material, the vapor pressures of the components in the feed, the reflux rate, column head pressure, pressure drop per stage, etc. The computer-generated design can then be modified by specifying an increase in the number of theoretical stages in the rectifying zone. The software can then be used to predict the temperature (or ACN composition) of the various theoretical stages throughout the column. One can identify a particular column design and a set of operating conditions for it that produce the required sigmoidal temperature profile in the rectifying zone. The computer-generated column design can then be used to construct an actual column having the required number of theoretical stages by using either trays (generally 1.5 trays per theoretical stage) or using other construction such as packing, in which case the so-called HETP (height equivalent to a theoretical plate) must be determined (generally available from manufacturers of packing materials). Whatever particular column is constructed, it must be operated to achieve the required sigmoidal temperature profile in its rectifying zone. The required profile can be achieved empirically by using a series of thermocouples disposed at various points along the length of the column and varying the distillate withdrawal rate until the temperature readings of the various thermocouples throughout the rectifying zone show the required profile. Alternatively, one can use computer-generated temperature versus theoretical stage graphs to predict the temperature that exists at a preselected stage in the rectifying zone when the required sigmoidal profile is present. Then, one can operate the actual column by varying the distillate withdrawal rate while monitoring the temperature at a point in the rectifying zone of the column corresponding to the preselected stage to achieve the computer-predicted temperature.

The following nonlimiting examples illustrate the present invention.

EXAMPLE 1

A 55 plate Oldershaw column was used throughout this study. Thermocouples were located at the top of the column, on trays 10, 25, and 35, and in the reboiler. Tray 1 is at the top of the column, and the tray numbers increase from top to bottom of the column. Feed points were located at trays 10, 25, and 35. Experiments were run using all three feed point locations, and for each feed point location, the column temperature profile was varied by adjusting the control temperature of one of the trays in the column. In all of these studies, the reflux ratio was maintained at 3.0, and the column head pressure at 150 mm Hg. The feed composition was 17% HMD, 73% ACN, 10% ADN, and 1500 ppm PRI.

In the discussion above, the term "stage" is used to describe a single equilibrium or theoretical stage. One theoretical stage is equivalent to 1.5 Oldershaw trays. Thus the column used in this study contained 37 theoretical stages.

In this first example the feed was to tray 25. In RUN 1 (not in accordance with the present invention) the temperature of tray 35 was controlled at 175 C. This kept the temperature profile low in the column, and corresponds to Curve 1 of FIG. 2. In RUN 2 (in accordance with the present invention), the temperature of tray 10 was controlled at 153 C., which gave a sigmoidal temperature profile above the fed point, corresponding to Curve 2 of FIG. 2. The tray temperatures and PRI contents of the distillate for these two cases are given in Table 1 below:

TABLE 1

Effect of Column Temperature Profile on PRI Content of Distillate

Tray Temperatures (C)

| RUN | T10 | T25 | T35 | PRI in Distillate (ppm) |
|---|---|---|---|---|
| 1 | 148 | 168 | 175 | 118 |
| 2 | 153 | 176 | 188 | 15 |

Example 1 shows that when the temperature profile is shifted up the column to provide a sigmoidal temperature profile above the feed tray, it is accompanied by a significant reduction in the PRI content of the HMD distillate, namely a reduction from 118 ppm to 15 ppm.

EXAMPLE 2

This example is identical to Example 1, with the exception that in this case the feed was to tray 35. In RUN 1 (not in accordance with the present invention), the temperature of tray 35 was controlled at 170 C., which kept the temperature profile low in the column, similar to Curve 1 in FIG. 2. In RUN 2 (in accordance with the present invention), the temperature of tray 25 was controlled at 157 C., which gives the sigmoidal temperature profile above the feed point, similar to Curve 2 of FIG. 2. The tray temperatures and distillate PRI contents are given in Table 2:

TABLE 2

Effect of Column Temperature Profile on PRI Content of Distillate

Tray Temperatures (C)

| RUN | T10 | T25 | T35 | PRI in Distillate (ppm) |
|---|---|---|---|---|
| 1 | 146 | 151 | 170 | 105 |
| 2 | 147 | 157 | 181 | 20 |

As in Example 1, shifting the temperature profile up the column creates the desired sigmoidal temperature profile above the feed point which reduces the PRI content of the HMD distillate. Adding 10 trays above the feed point in Example 2 gives no further reduction in PRI level of the distillate, but it does allow the ACN content of the distillate to be significantly reduced.

EXAMPLE 3

This example is identical to Example 1, except that the feed point was moved to tray 10. With this limited number of trays above the feed point it is impossible to develop the necessary sigmoidal temperature profile above the feed point. Thus, it is impossible to obtain distillate with the requisite low level of PRI. Table 3 shows the results for two temperature profiles.

TABLE 3

Effect of Column Temperature Profile on PRI Content of Distillate

Tray Temperatures (C)

| T10 | T25 | T35 | PRI in Distillate (ppm) |
|---|---|---|---|
| 140 | 173 | 188 | 54 |
| 141 | 183 | 189 | 60 |

In both of these cases, the necessary sigmoidal temperature profile above the feed point did not exist, and the level of PRI was higher than that obtained when the desired profile exists.

What is claimed is:

1. A process for separating HMD from a feed mixture comprising HMD, ACN and PRI, said process comprising:

a) introducing the feed mixture into a distillation column at a feed point located therein;

b) withdrawing from a distillate withdrawal point, located above the feed point, a distillate which comprises HMD, and which further comprises at most a minor portion of the PRI which is fed to the column in the feed mixture, the locations of the feed point and the distillate withdrawal point defining a rectifying zone of the column having a length which extends between the feed point and the distillate withdrawal point and a temperature which varies along the length; and c) withdrawing from a bottoms withdrawal point, located below the feed point, a bottoms which comprises ACN, substantially free of HMD, and which further comprises a major portion of the PRI fed to the column in the feed mixture;

provided that the process is carried out while the temperature in the rectifying zone of the column varies sigmoidally along the length of the rectifying zone.

* * * * *